United States Patent [19]

Yanagi et al.

[11] 4,189,350

[45] Feb. 19, 1980

[54] PROCESS FOR PURIFYING UROKINASE

[75] Inventors: Hideki Yanagi, Toyonaka; Yasuo Bai, Sakai; Junichi Yoshikawa; Shigeo Ogino, both of Nishinomiya, all of Japan

[73] Assignee: Sumitomo Chemical Company, Limited, Osaka, Japan

[21] Appl. No.: 911,475

[22] Filed: Jun. 1, 1978

[30] Foreign Application Priority Data

Jun. 3, 1977 [JP] Japan .................................. 52-65975

[51] Int. Cl.$^2$ ............................................. C07G 7/026
[52] U.S. Cl. .................................................... 435/215
[58] Field of Search ....................................... 195/66 B

[56] References Cited

U.S. PATENT DOCUMENTS 3,957,582 5/1976 Stried et al. ......................... 195/66 B
4,025,390 5/1977 Urakawa et al. .................. 195/66 B

*Primary Examiner*—Lionel M. Shapiro
*Attorney, Agent, or Firm*—Stevens, Davis, Miller & Mosher

[57] ABSTRACT

A process for purifying urokinase by contacting a crude urokinase-containing solution with a strongly acidic cation exchanger having sulfonic acid groups and adjusted to the $NH_4^+$ type to adsorb urokinase on said cation exchanger and then eluting urokinase from said exchanger, characterized in that urea is previously added to the crude urokinase-containing solution in such a rate that the final molar concentration of urea in the solution is 3 to 8 M. This process is capable of providing purified urokinase having substantially constant and high specific activity from a crude urokinase-containing solution with a high recovery regardless of purity of the crude urokinase.

3 Claims, No Drawings

PROCESS FOR PURIFYING UROKINASE

This invention relates to a process for purifying urokinase. More particularly, it relates to a process for recovering highly purified urokinase in a high yield, regardless of purity of crude urokinase used, from a crude urokinase-containing solution to which urea has been previously added in such a rate that the final molar concentration of urea in the solution is 3 to 8 M, which process comprises contacting said crude urokinase-containing solution with a strongly acidic cation exchanger having sulfonic acid groups and adjusted to the $NH_4^+$ type to adsorb urokinase specifically on said exchanger and then eluting the adsorbed urokinase from said exchanger.

Urokinase is an enzyme which is capable of deriving plasmin, a fibrinolytic enzyme, from plasminogen, and it is known that this substance is not only useful for the treatment of various kinds of thromboses but also capable of remarkably enhancing potency of the carcinostatic agents when used together with said agents. Urokinase isolated from human urine is free from harmful adverse effects such as antigen-antibody reaction and is now generally used with high efficacy.

Various methods have hitherto been used for purification of crude urokinase, for example, the methods using various kinds of weakly acidic cation exchangers or weakly basic anion exchangers or gel filtering agents such as crosslinked dextran. However, any of these methods is not necessarily satisfactory in respects of yield and purity of product, and more advantageous methods have been investigated.

The present inventors have made extensive studies on a more advantageous method for purification of urokinase, and as the results, found such a new finding that when urea is added to a crude urokinase-containing solution in such a rate that the final molar concentration of urea in the solution is 3 to 8 M and then the resulting solution is contacted with a strongly acidic cation exchanger having sulfonic acid groups and adjusted to the $NH_4^+$ type, urokinase is specifically adsorbed on said exchanger, resulting in a remarkable decrease of the rate of non-adsorbed urokinase as compared with the case where no urea is added to the crude urokinase-containing solution, so that, by eluting the adsorbed urokinase with an alkaline solution or other salt solutions, a purified urokinase having substantially constant and higher specific activity can be obtained with a higher recovery regardless of purity of the crude urokinase. The present invention has been accomplished based on this finding.

The strongly acidic cation exchangers having sulfonic acid groups used in this invention are of the type prepared by introducing sulfonic acid groups into a synthetic resin having a three-dimensional network structure such as polystyrene resin or phenol-formalin resin, for example, Dowex 50W, etc., manufactured by Dow Chemical Company; Amberlite IR-120B, CG-120, etc., manufactured by Rohm and Haas Company; and Duolite C-20, etc., manufactured by Diamond Shamrock Company; or the type prepared by introducing sulfoethyl or sulfopropyl groups into cellulose or crosslinked dextran, for example SE-cellulose manufactured by Serva Entwicklungslabor, etc. or SP-Sephadex manufactured by Pharmacia Fine Chemicals. Any of these are commercially available.

The process for purification of urokinase according to this invention is as follows.

A crude urokinase-containing solution adjusted to pH 4 to 9, preferably 6 to 8, to which urea is added in advance in such a rate that the final molar concentration of urea in the solution is 3 to 8 M, is contacted with a strongly acidic cation exchanger having sulfonic acid groups and adjusted to the $NH_4^+$ type to adsorb urokinase specifically on said cation exchanger. Such contact can be accomplished according to either a batchwise or column type operation. Adjustment of said cation exchanger to the $NH_4^+$ type can be attained by the commonly used means, that is, an ammonium chloride solution is contacted with said $H^+$ type cation exchanger and, after confirming that all the $H^+$ ions have been replaced with $NH_4^+$ ions by a pH measurement, said exchanger is washed with distilled water. The desired pH adjustment of the crude urokinase-containing solution can be effected by using a buffer solution such as phosphate buffer solution. The urokinase-adsorbed cation exchanger is washed with water or a low-concentration salt solution to remove a large portion of the impurities including urea other than urokinase. Then, urokinase adsorbed on said ion exchanger can be easily eluted with an alkaline solution or a high-concentration salt solution or a combination thereof. Dilute ammonia water or a buffer solution having pH of 10 to 12 can be used as the alkaline solution for said purpose, and an ammonium chloride solution or the like can be used as the salt solution. It is also possible to use an alkaline solution having pH of 8 to 12 containing a salt such as ammonium chloride.

A comparison between the case where urea was added to a crude urokinase-containing solution according to the process of this invention and the case where no urea was added is shown below as Referential Example. In this Example, Dowex 50W×8 was used as the strongly acidic cation exchanger having sulfonic acid groups and urokinase activity was measured according to the Ploug's fibrin plate method (Ploug et al: Biochim. Biophys. Acta, Vol. 24, page 278, 1957).

Referential Example

To 4 ml of a solution containing 11900 IU (international unit) of crude urokinase having a specific activity of 820 IU/mg protein, which had been dialyzed in advance against 0.1 M phosphate buffer solution having pH of 6.5 and containing 0.1 M of sodium chloride, was added 1.2 g or 2.0 g of urea, respectively. In addition, the same solution as above containing no ureas was prepared. Each solution thus prepared was passed through a column packed with 5 ml of Dowex 50W×8 (200–400 mesh) adjusted to the $NH_4^+$ type to adsorb urokinase. Thereafter said column was washed with 25 ml of distilled water and then urokinase was eluted with 3 ml of 4% ammonia water. The properties of the thus obtained urokinase are shown in Table 1 below.

Table 1

| Urea added (g) | Non-adsorbed urokinase (%) | Eluted urokinase Specific activity IU/mg | Eluted urokinase Recovery (%) |
|---|---|---|---|
| 0 | 20.3 | 8,990 | 66.0 |
| 1.2 | 6.1 | 15,500 | 81.0 |
| 2.0 | 4.6 | 17,100 | 74.3 |

The results of this Referential Example point evidently to the prominent effect by the addition of urea according to the present invention in decreasing the rate of non-adsorbed urokinase and increasing specific activity as well as recovery of eluted urokinase.

The present invention is further explained in detail by way of the following examples, but the present invention is not limited thereto.

EXAMPLE 1

26.3 g of urea was gradually added to 54 ml of a solution containing 314,000 IU of crude urokinase having specific activity of 1,080 IU/mg protein which had been dialyzed in advance against phosphate buffer solution having pH of 6.5 and containing 0.1 M of sodium chloride, and the resulting solution was passed through a column (2.8$\phi \times$25 cm) packed with Dowex 50W$\times$8 (200–400 mesh) adjusted to the $NH_4^+$ type to adsorb urokinase. After washing the column with 900 ml of distilled water, 160 ml of 4% ammonia water was passed through the column to elute urokinase, and the fraction having the urokinase activity was recovered. The thus obtained urokinase had total activity of 235,000 IU and specific activity of 18,200 IU/mg protein and was purified 16.9—fold over crude urokinase. The activity recovery was 74.8%.

EXAMPLE 2

87.8 g of urea was added to 180 ml of a solution containing 298,000 IU of crude urokinase having specific activity of 560 IU/mg protein, which had been dialyzed in advance as in Example 1, and the resulting solution was passed through a column (2.8$\phi \times$25 cm) packed with Dowex 50W$\times$8 (200–400 mesh) adjusted to the $NH_4^+$ type to adsorb urokinase. After washing the column with 900 ml of distilled water, urokinase was eluted with 160 ml of 4% ammonia water and the fraction having the urokinase activity was recovered. The thus obtained urokinase had total activity of 239,000 IU and specific activity of 17,000 IU/mg protein and was purified 30.4—fold over crude urokinase. The activity recovery was 80.2%.

The above results show the fact that even when using crude urokinase having about half the specific activity of that used in Example 1, it is possible to recover purified urokinase having substantially same degree of high specific activity as that obtained in Example 1.

EXAMPLE 3

53.6 g Of urea was added to 110 ml of a solution containing 140,000 IU of crude urokinase having specific activity of 660 IU/mg protein, which had been dialyzed in advance as in Example 1, and the resulting solution was passed through a column (2.8$\phi \times$25 cm) of Duolite C-20 adjusted to the $NH_4^+$ type to adsorb urokinase. After washing the column with 750 ml of distilled water, urokinase was eluted with 150 ml of 4% ammonia water and the fraction having the urokinase activity was recovered. The thus obtained urokinase had total activity of 96,600 IU and specific activity of 13,600 IU/mg protein and was purified 20.6—fold over crude urokinase. The activity recovery was 69.0%.

What is claimed is:

1. A process for purifying urokinase by contacting a crude urokinase-containing solution with a strongly acidic cation exchanger having sulfonic acid groups and adjusted to the $NH_4^+$ type to adsorb urokinase and then eluting the adsorbed urokinase from said exchanger, characterized in that urea is previously added to said crude urokinase-containing solution in such a rate that the final molar concentration of urea in the solution is 3 to 8 M.

2. A process according to claim 1, wherein pH of the crude urokinase-containing solution is within the range of 4 to 9.

3. A process according to claim 1, wherein the cation exchanger is polystyrene resin or phenol-formalin resin having sulfonic acid groups, or cellulose or crosslinked dextran having sulfoethyl groups or sulfopropyl groups.

* * * * *